(12) United States Patent
Winski

(10) Patent No.: US 10,279,140 B2
(45) Date of Patent: May 7, 2019

(54) HUMIDITY CONTROL LIQUID MAXIMIZATION PRESSURE SUPPORT DEVICE

(71) Applicant: KONINKLIJKE PHILIPS N.V., Eindhoven (NL)

(72) Inventor: Jeffrey Ronald Winski, Irwin, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 981 days.

(21) Appl. No.: 14/649,032

(22) PCT Filed: Dec. 17, 2013

(86) PCT No.: PCT/IB2013/061013
§ 371 (c)(1),
(2) Date: Jun. 2, 2015

(87) PCT Pub. No.: WO2014/102660
PCT Pub. Date: Jul. 3, 2014

(65) Prior Publication Data
US 2015/0306335 A1    Oct. 29, 2015

Related U.S. Application Data
(60) Provisional application No. 61/746,796, filed on Dec. 28, 2012.

(51) Int. Cl.
*A61M 16/16*    (2006.01)
*A61M 16/06*    (2006.01)
(Continued)

(52) U.S. Cl.
CPC ........ *A61M 16/16* (2013.01); *A61M 16/0003* (2014.02); *A61M 16/0057* (2013.01);
(Continued)

(58) Field of Classification Search
CPC .............. A61M 16/1085; A61M 16/16; A61M 16/161; A61M 16/162; A61M 2205/3386;
(Continued)

(56) References Cited

U.S. PATENT DOCUMENTS 6,095,505 A * 8/2000 Miller ............... A61M 16/1075
128/203.27
6,105,575 A 8/2000 Estes et al.
(Continued)

FOREIGN PATENT DOCUMENTS

| WO | 2011057362 A1 | 5/2011 |
|---|---|---|
| WO | 2011078706 A2 | 6/2011 |
| WO | 2011136665 A1 | 11/2011 |

*Primary Examiner* — Colin W Stuart
*Assistant Examiner* — Douglas Y Sul

(57) ABSTRACT

A pressure support system configured to provide pressure support therapy to a subject is described. The pressure support system comprises a humidifier configured to control the humidity of gas provided to the subject during a sleep cycle to ensure an amount of liquid will remain in the humidifier at the conclusion of an estimated usage time. The pressure support system is configured to ensure humidified breathing gas is delivered to a subject during a usage time within a pressure support usage period. During times when the subject's moisture demand is greater than amount of moisture available in the humidifier, the pressure support system may decrease the amount moisture in the breathing gas so humidified therapy is available during the entire time the user is asleep.

18 Claims, 2 Drawing Sheets

(51) Int. Cl.
  *A61M 16/10* (2006.01)
  *A61M 16/00* (2006.01)
  *A61B 5/087* (2006.01)
  *A61B 5/00* (2006.01)

(52) U.S. Cl.
  CPC .......... *A61M 16/024* (2017.08); *A61M 16/06* (2013.01); *A61M 16/109* (2014.02); *A61B 5/087* (2013.01); *A61B 5/7275* (2013.01); *A61M 16/0069* (2014.02); *A61M 16/0072* (2013.01); *A61M 16/0075* (2013.01); *A61M 16/0666* (2013.01); *A61M 16/1085* (2014.02); *A61M 16/1095* (2014.02); *A61M 2205/18* (2013.01); *A61M 2205/3317* (2013.01); *A61M 2205/3334* (2013.01); *A61M 2205/3351* (2013.01); *A61M 2205/3365* (2013.01); *A61M 2205/3368* (2013.01); *A61M 2205/3375* (2013.01); *A61M 2205/3379* (2013.01); *A61M 2205/3389* (2013.01); *A61M 2205/3553* (2013.01); *A61M 2205/3584* (2013.01); *A61M 2205/3592* (2013.01); *A61M 2205/3653* (2013.01); *A61M 2205/50* (2013.01); *A61M 2205/505* (2013.01); *A61M 2205/52* (2013.01)

(58) Field of Classification Search
  CPC .. A61M 2205/3389; A61M 2205/3379; A61M 2205/3334; A61M 2205/3368; G05D 22/02; G05D 22/00; F24F 11/0008; F24F 6/08; F24F 6/10; F24F 6/25
  See application file for complete search history.

(56) References Cited

U.S. PATENT DOCUMENTS

| | | |
|---|---|---|
| 2007/0169776 A1 | 7/2007 | Kepler et al. |
| 2012/0125333 A1* | 5/2012 | Bedford ................ A61M 16/06 128/203.25 |
| 2013/0081701 A1* | 4/2013 | Korneff ..................... F15D 1/12 137/2 |
| 2013/0174841 A1* | 7/2013 | McAuley .......... A61M 16/0066 128/203.14 |
| 2015/0014874 A1 | 1/2015 | Winski |
| 2015/0020801 A1* | 1/2015 | Frame ............... A61M 16/0057 128/202.22 |

* cited by examiner

HUMIDITY CONTROL LIQUID MAXIMIZATION PRESSURE SUPPORT DEVICE

CROSS-REFERENCE TO PRIOR APPLICATIONS

This application is the U.S. National Phase application under 35 U.S.C. § 371 of International Application Serial No. PCT/IB2013/061013, filed on Dec. 17, 2013, which claims the benefit of U.S. Application Ser. No. 61/746,796, filed on Dec. 28, 2012. These applications are hereby incorporated by reference herein.

BACKGROUND

1. Field

The present disclosure pertains to a pressure support system configured to provide pressure support therapy to a subject, wherein the pressure support system comprises a humidifier configured to control the humidity of gas provided to the subject during a sleep cycle to ensure an amount of liquid will remain in the humidifier at the conclusion of an estimated usage time.

2. Description of the Related Art

Pressure support systems that provide pressure support therapy to the airway of a subject are known. Some conventional pressure support systems include humidifiers configured to control the level of humidity of gas provided to the subject during pressure support therapy.

Humidifiers are commonly used with ventilators, pressure support systems, and other respiratory therapy devices to add humidity to the gas being supplied to a subject. The humidity added to the gas supplied to the subject by a conventional ventilator or pressure support system is typically monitored and/or controlled in a feedback loop to provide a consistent humidity level. Typically, these systems are configured to determine a target humidity output and set a humidifier heating element temperature to achieve the target humidity. Such systems do not take into account the time the therapy device has been active, the amount of water in the humidifier, or the number of hours a patient sleeps nightly. A humidifier that runs out of water while the pressure support system is still operating may result in delivery of a hot, dry gas to the subject, leading to a dry and sore mucus membrane that can lead to other medical issues.

SUMMARY

Accordingly, one or more aspects of the present disclosure relate to a pressure support system configured to provide humidity controlled pressure support to a subject. In some embodiments, the pressure support system comprises a pressure generator configured to generate a pressurized flow of breathable gas for delivery to the airway of a subject; a humidifier configured to hold a volume of liquid and controllably elevate the temperature of the liquid such that vapor formed from the heated liquid humidifies the pressurized flow of breathable gas; one or more usage time sensors configured to generate output signals conveying information related to one or more usage time parameters; and one or more processors configured to execute computer program modules. The computer program modules comprise a liquid level module configured to obtain a level of the liquid held by the humidifier; a usage time module configured to estimate the usage time of the subject for a current usage session based on the output signals generated by the one or more usage time sensors; and a humidifier control module configured to control the humidifier to heat the liquid based on the estimated usage time for the current usage session and the level of the liquid held by the humidifier, thereby ensuring an amount of liquid will remain in the humidifier at the conclusion of the estimated usage time.

Yet another aspect of the present disclosure relates to a method of delivering a humidity controlled pressurized flow of breathable gas to the airway of a subject. The method comprises generating a pressurized flow of breathable gas for delivery to the airway of a subject; humidifying the pressurized flow of breathable gas by holding a volume of liquid in a humidifier, and controllably elevating the temperature of the liquid within the humidifier to heat the liquid such that vapor formed from the heated liquid humidifies the pressurized flow of breathable gas; generating output signals conveying information related to one or more usage time parameters; obtaining a level of the liquid held by the humidifier; estimating the usage time of the subject for a current usage session based on the output signals conveying information related to the usage time parameters; and controlling the humidifier to heat the liquid based on the estimated usage time for the current usage session and the level of the liquid held by the humidifier, thereby ensuring an amount of liquid will remain in the humidifier at the conclusion of the estimated usage time.

Still another aspect of the present disclosure relates to a pressure support system configured to provide humidity controlled pressure support to a subject. In some embodiments, the pressure support system comprises means to generate a pressurized flow of breathable gas for delivery to the airway of a subject; means to hold a volume of liquid and controllably elevate the temperature of the liquid such that vapor formed from the heated liquid humidifies the pressurized flow of breathable gas; means to generate output signals conveying information related to one or more usage time parameters; and means to execute computer program modules, the computer program modules comprising means to obtain a level of the liquid held by the means to humidify, means to estimate the usage time of the subject for a current usage session based on the output signals from the means to generate output signals conveying information related to one or more usage time parameters, and means to control the means to humidify based on the estimated usage time for the current usage session and the level of the liquid held by the means to humidify, thereby ensuring an amount of liquid will remain in the means to humidify at the conclusion of the estimated usage time.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
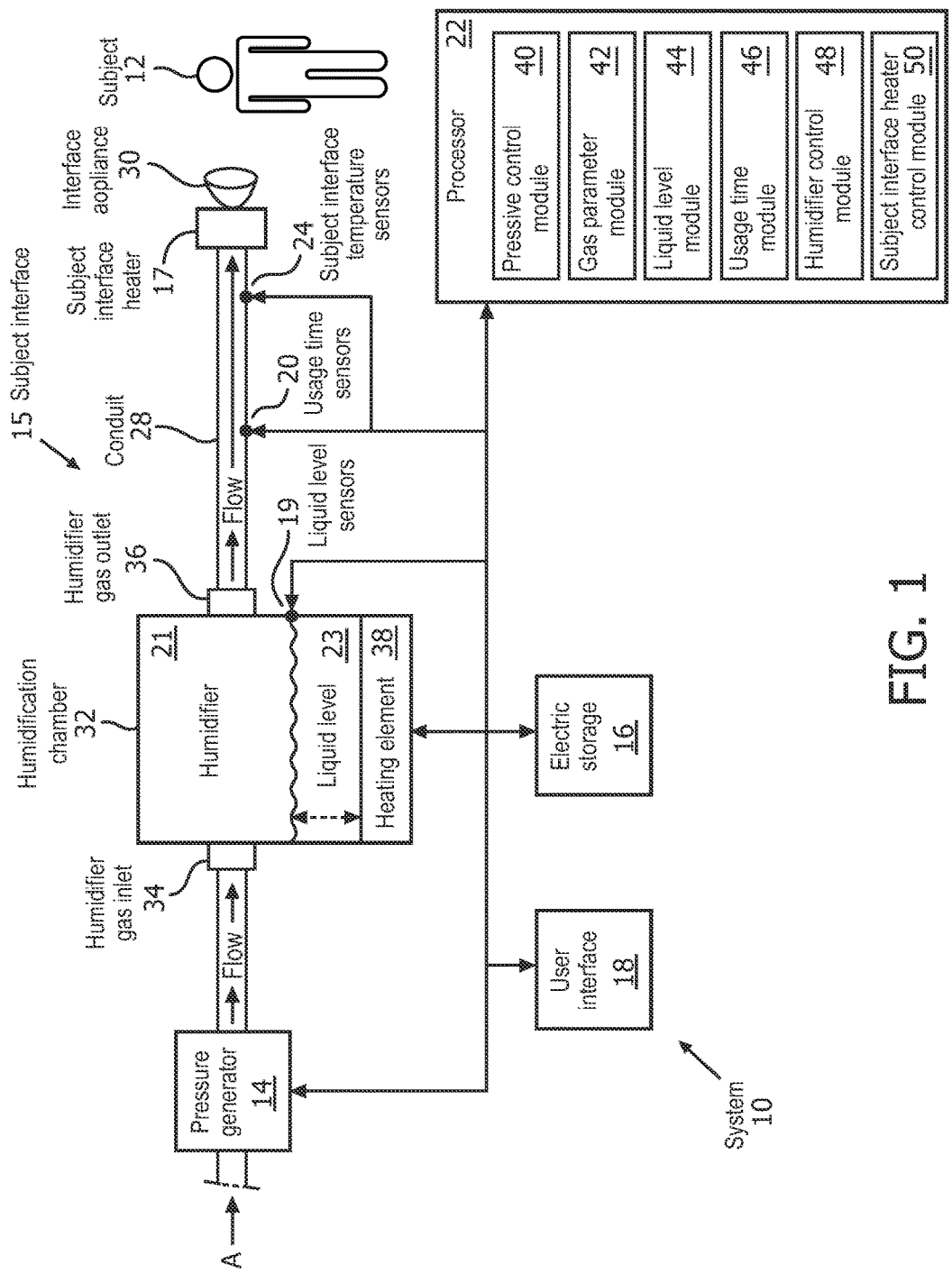
FIG. 1 is a pressure support system configured to provide humidity controlled pressure support to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a pressure support system 10 configured to provide pressure support therapy to a subject 12. Pressure support system 10 is configured to provide the pressure support therapy in the form of a flow of gas that is delivered to the airway of the subject. The pressure support therapy may be dynamic in that one or more parameters of the flow of gas generated by pressure support system 10 may be adjusted based on detection of one or more parameters. For example, pressure of the flow of gas may be increased based on changes to one or more parameters that indicate a respiratory event (e.g., an apnea, snoring, etc.).

Pressure support system 10 is configured to ensure humidified breathing gas is delivered to subject 12 during a pressure support system usage time period. Pressure support system usage time may comprise one or both of the total time subject 12 is connected to system 10 during a usage session, and/or the time subject 12 is asleep while connected to system 10 during a usage session. During uses when the subject's anticipated moisture demand for a usage session is greater than amount of moisture available in the humidifier, pressure support system 10 may decrease the amount moisture in the breathing gas so humidified therapy is available during the entire time subject 12 uses system 10.

In one embodiment, pressure support system 10 comprises one or more of a pressure generator 14, a subject interface 15, a subject interface heater 17, electronic storage 16, a user interface 18, one or more liquid level sensors 19, one or more usage time sensors 20, a humidifier 21, a processor 22, and/or other components. Although FIG. 1 shows humidifier 21 downstream of pressure generator 14, the positioning of the two components may be switched in some embodiments, in which case humidifier 21 would be positioned upstream of pressure generator 14.

In some embodiments, pressure generator 14 is configured to generate a flow of gas for delivery to the airway of subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, such as the ambient atmosphere, as indicated by arrow A in FIG. 1 and elevates the pressure of that gas for delivery to the airway of a patient. Pressure generator 14 is any device, such as, for example, a pump, blower, piston, or bellows, that is capable of elevating the pressure of the received gas for delivery to a patient. The present disclosure also contemplates that gas other than ambient atmospheric air may be introduced into subject interface 15 for delivery to the patient. In such embodiments, a pressurized canister or tank of gas containing air, oxygen, and/or another gas may supply the intake of pressure generator 14. In some embodiments, pressure generator 14 need not be provided, but instead the gas may be pressurized by the pressure of the canister and/or tank of pressurized gas itself.

In one embodiment, pressure generator 14 is a blower that is driven at a substantially constant speed during the course of the pressure support treatment to provide the gas in subject interface 15 with a substantially constant elevated pressure and/or flow rate. Pressure generator 14 may comprise a valve for controlling the pressure/flow of gas. The present disclosure also contemplates controlling the operating speed of the blower, either alone or in combination with such a valve, to control the pressure/flow of gas provided to the patient. An example of a pressure support system suitable for use in the present disclosure is described in U.S. Pat. No. 6,105,575, hereby incorporated by reference in its entirety.

The flow of gas is delivered to the airway of a subject 12 from pressure generator 14 via subject interface 15. Subject interface 15 is configured to communicate the pressurized flow of gas generated by pressure generator 14 to the airway of subject 12. As such, subject interface 15 comprises one or more conduits 28, an interface appliance 30, and/or other components. Conduits 28 are configured to convey the pressurized flow of gas to interface appliance 30. Interface appliance 30 is configured to deliver the flow of gas to the airway of subject 12. In some embodiments, interface appliance 30 is non-invasive. As such, interface appliance 30 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 30. Some examples of non-invasive interface appliance 30 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Although subject interface 15 is illustrated in FIG. 1 as a single-limbed circuit for the delivery of the flow of gas to the airway of the subject, this is not intended to be limiting. The scope of this disclosure comprises double-limbed circuits having a first limb configured to both provide the flow of gas to the airway of the subject, and a second limb configured to selectively exhaust gas from subject interface 15 (e.g., to exhaust exhaled gases).

Subject interface heater 17 is configured to controllably heat the pressurized flow of breathable gas in subject interface 15. Subject interface heater 17 is illustrated in FIG. 1 at a single location within (or in communication with) conduit 28, near interface appliance 30, and/or within interface appliance 30. The illustrated position of subject interface heater 17 is not intended to be limiting. Subject interface heater 17 may be located in any position that allows it to controllably heat the pressurized flow of breathable gas in subject interface 15. Subject interface heater 17 may be configured to heat the pressurized flow of breathable gas continuously along the entire length of conduit 28. Subject interface heater 17 may be configured to heat the pressurized flow of breathable gas by dissipating electrical current (e.g., resistive heating). Subject interface heater 17 may comprise one or more of a heating coil, a heating jacket, heating tape, and/or other heating devices. Subject interface heater 17 may be configured to heat the gas in subject interface 15 directly and/or indirectly. In some embodiments, a heating coil may be positioned within conduit 28 in fluid communication with the pressurized flow of breathable gas to directly heat the gas flow. In some embodiments, a heating jacket may be placed around conduit 28 to heat the flow of gas indirectly by transferring heat through the wall of conduit 28. System 10 may, in some embodiments, not include any subject interface heater 17.

In some embodiments, electronic storage 16 comprises electronic storage media that electronically stores information. The electronic storage media of electronic storage 16 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., user interface 18, processor 22, etc.).

By way of a non-limiting example, electronic storage 16 may be configured to store information related to patient usage time and/or humidifier liquid usage, wherein humidifier liquid usage is the amount of liquid from humidifier 21 subject 12 uses while receiving therapy from system 10. Electronic storage 16 may store individual nightly information and/or information representative of multiple nights (e.g., average sleep time, maximum sleep time, minimum sleep time). In this example, stored information that is representative of an individual night and/or multiple nights may be used to estimate future sleep and/or future humidifier liquid usage.

User interface 18 is configured to provide an interface between system 10 and subject 12 and/or another user (e.g., a doctor, care-giver, etc.) through which subject 12 may provide information to and receive information from system 10. This enables data, cues, results, and/or instructions and any other communicable items, collectively referred to as "information," to be communicated between subject 12 and one or more of pressure generator 14, electronic storage 16, processor 22, and/or other components of system 10. Examples of interface devices suitable for inclusion in user interface 18 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 comprises a plurality of separate interfaces. In one embodiment, user interface 18 comprises at least one interface that is provided integrally with pressure generator 14.

It is to be understood that other communication techniques, either hard-wired or wireless, are also contemplated by the present disclosure as user interface 18. For example, the present disclosure contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 comprise, but are not limited to, an RS-232 port, RF link, an IR link, modem (telephone, cable or other). In short, any technique for communicating information with system 10 is contemplated by the present disclosure as user interface 18.

Liquid level sensors 19 are configured to generate one or more output signals conveying information related to a current liquid level in humidifier 21. Liquid level sensors 19 may comprise one or more sensors that measure such parameters directly (e.g., through communication with the liquid in humidifier 21). Liquid level sensors 19 may comprise one or more sensors that generate output signals related to a current liquid level in humidifier 21 indirectly. For example, liquid level sensors 19 may comprise one or more sensors configured to generate an output based on an operating parameter of humidifier 21 (e.g., a current drawn, voltage, and/or other operating parameters), and/or other sensors. In this manner, liquid level sensors 19 may indirectly sense liquid level in humidifier 21 through estimation. Liquid level sensors 19 may comprise one or more of a float switch, a pressure sensor, an ultrasonic sensor, a heat capacity based sensor, and/or other liquid level sensors. An example of a heat capacity based sensor suitable for use in the present disclosure is described in U.S. Patent Application Ser. No. 61/605,240 filed Mar. 1, 2012, hereby incorporated by reference in its entirety.

Although liquid level sensors 19 are illustrated in FIG. 1 at a single location in system 10, this is not intended to be limiting. Liquid level sensors 19 may comprise sensors disposed in a plurality of locations, such as for example, at various locations within (or in communication with) humidifier 21, and/or other locations.

Usage time sensors 20 are configured to generate one or more output signals conveying information related to one or more usage time parameters. The one or more usage time parameters may comprise parameters related to the total time subject 12 spends connected to system 10 during a usage session, and/or time subject 12 is asleep while connected to system 10 during a usage session. The one or more usage time parameters may comprise one or more gas parameters of the pressurized flow of breathable gas, breathing parameters related to respiration of subject 12, and/or other parameters. Usage time sensors 20 may comprise one or more sensors that measure such parameters directly (e.g., through fluid communication with the flow of gas in conduit 28). Usage time sensors 20 may comprise one or more sensors that generate output signals related to the one or more usage time parameters indirectly. For example, usage time sensors 20 may comprise one or more sensors configured to generate an output based on an operating parameter of pressure generator 14 (e.g., a valve driver or motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters.

Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. The one or more breathing parameters of subject 12 may comprise other parameters that provide information about the breathing of the subject. For example, usage time sensors 20 may comprise a transducer configured to detect acoustic waves transmitted to pressure support system 10 through subject interface 15. These acoustic waves may convey information related to respiratory effort of the subject, and/or the noise generated by the subject during respiration (e.g., during snoring).

Although usage time sensors 20 are illustrated in FIG. 1 at a single location in system 10, this is not intended to be limiting. Usage time sensors 20 may comprise sensors disposed in a plurality of locations, such as for example, at various locations within (or in communication with) conduits 28, within pressure generator 14, within humidifier 21, within (or in communication with) interface appliance 30, and/or other locations.

Subject interface temperature sensor(s) 24 are configured to generate one or more output signals conveying information related to the temperature of the pressurized flow of breathable gas in subject interface 15. Although sensor(s) 24 are illustrated in FIG. 1 at a single location in system 10, this is not intended to be limiting. Sensors 24 may comprise multiple sensors disposed in a plurality of locations within subject interface 15, such as for example, at various locations within (or in communication with) conduit 28, within (or in communication with) interface appliance 30, and/or other locations. Output signals generated by subject interface temperature sensors 24 may be transmitted wirelessly and/or via wires. Subject interface temperature sensor(s) 24 may be configured to directly sense the temperature of the pressurized flow of breathable gas in subject interface 15, or sensor(s) 24 may indirectly sense the temperature through estimation.

Humidifier 21 is configured to humidify the flow of gas in system 10. Humidifier 21 may comprise a humidification chamber 32, a gas inlet 34, a gas outlet 36, a heating element 38, and/or other components. In one embodiment, humidifier 21 is a warm mist humidifier (e.g., a vaporizer) configured to generate water vapor by heating liquid held within humidifier 21 via heating element 38. Humidifier 21 is configured such that the flow of gas is received from pressure generator 14 by humidifier 21 through gas inlet 34 and is humidified within humidification chamber 32 by the water vapor before being released from humidification chamber 32 through gas outlet 36. In one embodiment, gas outlet 36 is connected with subject interface 15 such that the humidified flow of gas is delivered to the airway of subject 12 through subject interface 15. U.S. Patent Application Publication No. 2007/0169776, incorporated herein by reference in its entirety, discloses an exemplary humidifier device suitable for use in the present disclosure. Humidifier devices having alternative designs may also be used.

Heating element 38 is configured to controllably elevate the temperature of liquid within humidification chamber 32. In some embodiments, heating element 38 is positioned at the bottom of humidification chamber 32 in proximity to the liquid in humidification chamber 32. The heat emitted by heating element 38 is dispensed directly into the liquid in humidification chamber 32. This emission of heat by heating element 38 into the liquid vaporizes the liquid.

Processor 22 is configured to provide information processing capabilities in system 10. As such, processor 22 may comprise one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may comprise a plurality of processing units. These processing units may be physically located within the same device (e.g., humidifier 21), or processor 22 may represent processing functionality of a plurality of devices operating in coordination.

As shown in FIG. 1, processor 22 is configured to execute one or more computer program modules. The one or more computer program modules may include one or more of a pressure control module 40, a gas parameter module 42, a liquid level module 44, a usage time module 46, a humidifier control module 48, a subject interface heater control module 50, and/or other modules. Processor 22 may be configured to execute modules 40, 42, 44, 46, 48, and/or 50 by software; hardware; firmware; some combination of software, hardware, and/or firmware; and/or other mechanisms for configuring processing capabilities on processor 22.

It should be appreciated that although modules 40, 42, 44, 46, 48, and 50 are illustrated in FIG. 1 as being co-located within a single processing unit, in implementations in which processor 22 includes multiple processing units, one or more of modules 40, 42, 44, 46, 48, and/or 50 may be located remotely from the other modules. The description of the functionality provided by the different modules 40, 42, 44, 46, 48, and/or 50 described below is for illustrative purposes, and is not intended to be limiting, as any of modules 40, 42, 44, 46, 48 and/or 50 may provide more or less functionality than is described. For example, one or more of modules 40, 42, 44, 46, 48 and/or 50 may be eliminated, and some or all of its functionality may be provided by other modules 40, 42, 44, 46, 48, and/or 50. As another example, processor 22 may be configured to execute one or more additional modules that may perform some or all of the functionality attributed below to one of modules 40, 42, 44, 46, 48, and/or 50.

Pressure control module 40 is configured to control pressure generator 14 to generate the flow of gas in accordance with the therapy regime. By way of non-limiting example, processor 22 may control pressure generator 14 such that the pressure support provided to the subject via the flow of gas comprises, non-invasive ventilation, positive airway pressure support, continuous positive airway pressure support, bi-level support, BiPAP®, and/or other types of pressure support therapy.

Gas parameter module 42 is configured to determine one or more gas parameters of the pressurized flow of breathable gas. Gas parameter module 42 is configured to determine the one or more gas parameters based on the output signals of usage time sensors 20. The one or more gas parameters of the pressurized flow of breathable gas may comprise, for example, one or more of a flow rate, a volume, a pressure, humidity, temperature, acceleration, velocity, and/or other gas parameters. The information determined by gas parameter module 42 may be used for estimating the usage time of subject 12 during a current usage session, and/or other uses.

Liquid level module 44 is configured to obtain the level 23 of the liquid held by humidifier 21. Determining liquid level 23 may include determining a volume of the liquid, a height at which the liquid surface sits, and/or other measurements of the amount of liquid held by humidifier 21. Liquid level 23 may be obtained by taking liquid level 23 to be the same at the beginning of each usage (e.g., a level programmed and/or stored at manufacture that corresponds to a line or other instruction presented to users with respect to how much liquid should be added before each sleep period), obtained responsive to information entered by a user via user interface 18 (e.g., the user indicates via user interface 18 that the humidifier is half filled with liquid), determined from the output signals generated by the one or more liquid level sensors 19, and/or obtained by another method.

In some embodiments, liquid level module 44 is further configured to determine a liquid usage rate during a current usage session. The liquid usage rate may be determined responsive to information entered by a user via user interface 18 (e.g., the user indicates via user interface 18 the rate at which the liquid is to be consumed), determined based on the output signals generated by one or more liquid level sensors 19, and/or determined by another method. By way of a non-limiting example, subject 12 and/or another user may fill humidifier 21 with liquid to a level indicated on humidifier 21 before going to sleep. Liquid level module 44 may obtain the starting liquid level in humidifier 21 from liquid level sensors 19. At one or more times during the usage period of subject 12, liquid level module 44 may obtain a current liquid level from liquid level sensors 19. The difference between the starting liquid level and the current liquid level, and the time between obtaining the levels, may be used to determine a liquid usage rate.

Usage time module 46 is configured to estimate the usage time of subject 12 for the current system 10 usage session. This estimate may include an estimation of the total time subject 12 will be connected to system 10 during the current usage session, an estimation of the time subject 12 will be asleep while connected to system 10 during the current usage session, and/or estimates of other periods of time during the current usage session. The usage time may be estimated based on information entered by a user via user interface 18, estimated based the output signals generated by the one or more usage time sensors 20, estimated based on the one or more gas parameters determined by gas parameter module 42, estimated based on data stored in electronic storage 16, and/or estimated by another method. In one embodiment, usage time module 46 estimates usage time based on previous respiration by subject 12 during the current usage period. For example, the usage time may be estimated based on a gas parameter determined by gas parameter module 42 for each inhalation in a previous series of consecutive inhalations.

In some embodiments, usage time module 46 may be configured to estimate the usage time of subject 12 based on a combination of one or more of the factors listed above. For example, usage time module 46 may determine that subject 12 has begun use based on output signals conveying breathing parameter information from usage time sensors 20. Usage time module 46 may then estimate the length of time subject 12 will remain asleep based on previous data stored in electronic storage 16 (e.g., the average length of time subject 12 slept during one or more previous sleep periods). Usage time module 46 may adjust the original estimated sleeping time while subject 12 is still sleeping based on an output signal from usage time sensors 20 indicating, for example, wakeful sleep by subject 12.

Humidifier control module 48 is configured to control humidifier 21 to heat the liquid in humidifier 21 to ensure an amount of liquid will remain in humidifier 21 at the conclusion of the estimated usage time. Humidifier control module 48 is configured to control humidifier 21 based on the estimated usage time for the current usage session and the amount of liquid held by humidifier 21. Humidifier control module 48 may be configured to control humidifier 21 to heat the liquid in humidifier 21 to maximize the humidity in the pressurized flow of breathable gas and/or to ensure an amount of liquid will remain in humidifier 21 at the conclusion of the estimated usage time. Humidifier control module 48 may be configured to adjust operation of humidifier 21 from an ordinary mode of operation to extend the time the pressurized flow of breathable gas is humidified during the current usage session. For example, during times when the subject's liquid demand for the current usage period is greater than the amount of liquid available in humidifier 21, humidifier control module 48 may decrease the amount moisture in the breathing gas so humidified therapy is available during the entire user sleep cycle.

By way of a non limiting example, humidifier control module 48 may calculate a projected liquid need based the usage time determined by usage time module 46 and the current liquid usage rate determined by liquid level module 44. Humidifier control module 48 may then compare the projected liquid need to the current amount of liquid in humidifier 21 sensed by liquid level sensors 19. Humidifier control module 48 may then decrease, and/or hold the rate at which the liquid in humidifier 21 is evaporated to ensure an amount of liquid remains in humidifier 21 at the conclusion of the estimated usage time.

Humidifier control module 48 may perform projected liquid need calculations according to one or more algorithms. The one or more algorithms may be programmed into processor 22 at manufacture, determined by a user via user interface 18, and/or determined by another method. Algorithm variables may comprise the amount of liquid in humidifier 21, estimated usage time, liquid usage rate, gas humidity, ambient humidity, conduit 28 temperature, and/or other variables.

System 10 and, in particular humidifier control module 48, may be configured so that the amount of liquid that is to remain in humidifier 21 at the conclusion of the estimated usage time may be zero or an amount other than zero. The amount of liquid that is to remain in humidifier 21 at the conclusion of the estimated usage time may also be selectable as zero or an amount other than zero by way of user interface 18.

Subject interface heater control module 50 is configured to control subject interface heater 17 to maintain the temperature of the pressurized flow of breathable gas at a target temperature. In some embodiments, subject interface heater control module 50 may determine a target temperature based on information entered by a user through user interface 18, based on output signals from subject interface temperature sensors 24, based on information from humidifier control module 48, and/or other methods. In some embodiments, responsive to humidifier control module 48 adjusting humidifier 21 from an ordinary mode of operation to extend the time the pressurized flow of breathable gas is humidified during the current usage session, subject interface heater control module 50 may adjust the temperature of the gas delivered to subject 12 to maintain a target humidity level determined by humidifier control module 48. For example, responsive to the rate at which liquid is evaporated by reduced by humidifier control module 48, subject interface heater control module 50 may be configured to decrease the temperature of the pressurized flow of breathable gas to maintain (or reduce changes to) a relative humidity of the pressurized flow of breathable gas.

Figure 2:
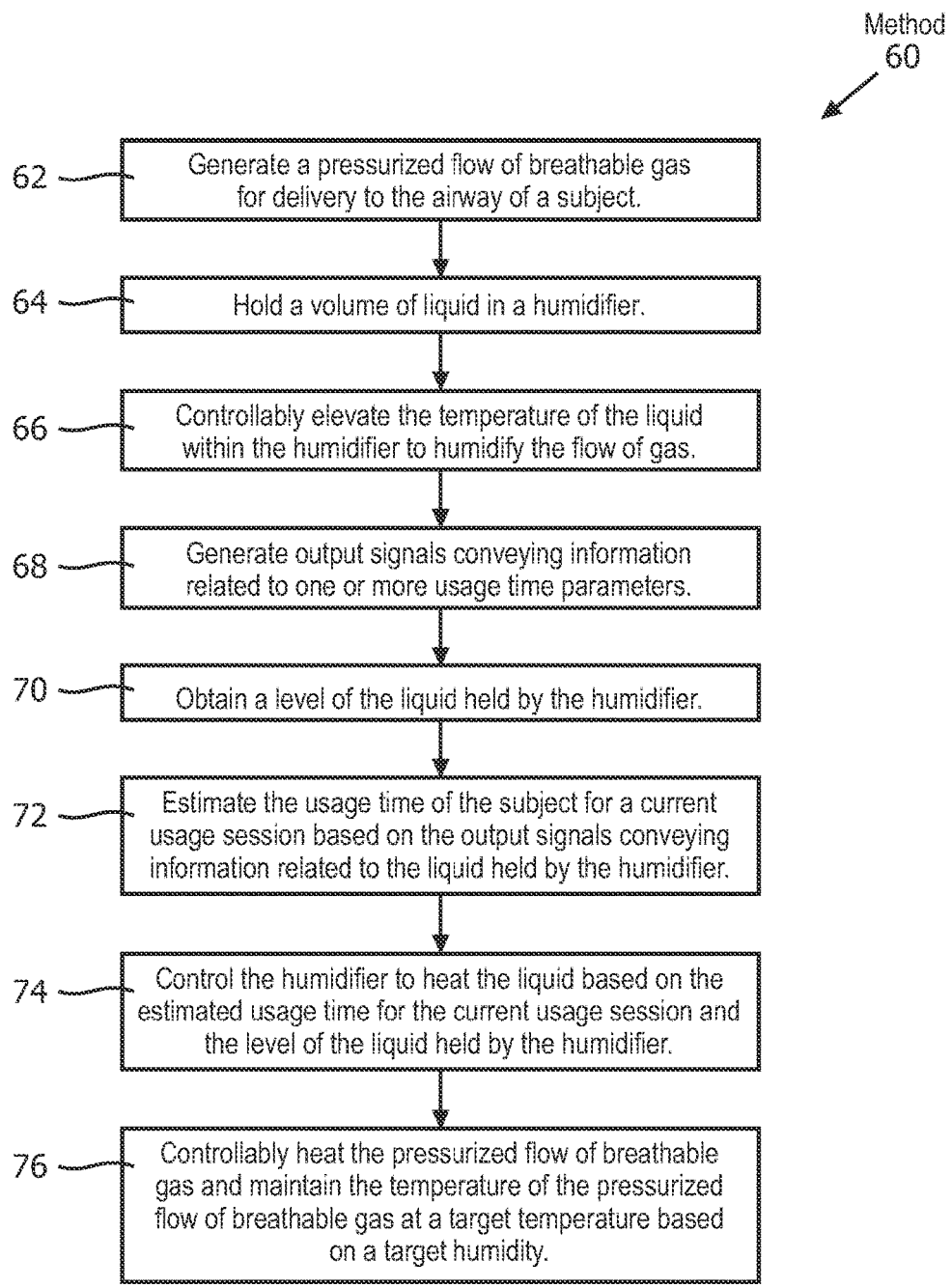
FIG. 2 is a method for providing humidity controlled pressure support to a subject.

FIG. 2 illustrates a method 60 of delivering a humidity controlled pressurized flow of breathable gas to the airway of a subject. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 2 and described below is not intended to be limiting.

In some embodiments, method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, a pressure generator generates a pressurized flow of breathable gas. In some embodiments, operation 62 is performed by a pressure generator the same as or similar to pressure generator 14 (shown in FIG. 1 and described herein).

At an operation 64, a volume of liquid is held in a humidifier. In some embodiments, operation 64 is performed by a humidifier the same as or similar to humidifier 21 (shown in FIG. 1 and described herein).

At an operation 66, the temperature of the liquid within the humidifier is controllably elevated to humidify the flow of gas. In some embodiments, operation 66 is performed by a humidifier the same as or similar to humidifier 21 (shown in FIG. 1 and described herein.)

At an operation 68, output signals conveying information related to one or more usage time parameters are generated. In some embodiments, operation 68 is performed by usage time sensors the same as or similar to usage time sensors 20 (shown in FIG. 1 and described herein.)

At an operation 70, a level of the liquid held by the humidifier is obtained. In some embodiments, operation 70 is performed by a liquid level module the same as or similar to liquid level module 44 (shown in FIG. 1 and described herein.)

At an operation 72, the usage time of the subject for a current usage session is estimated. The estimated usage time is based on the output signals conveying information related to the usage time parameters. In some embodiments, operation 72 is performed by a processor module the same as or similar to usage time module 46 (shown in FIG. 1 and described herein.)

At an operation 74, the humidifier is controlled to heat the liquid based on the estimated usage time for the current usage session and the level of the liquid held by the humidifier, thereby ensuring an amount of liquid will remain in the humidifier at the conclusion of the estimated usage time. In some embodiments, operation 74 is performed by a processor module the same as or similar to humidifier control module 48 (shown in FIG. 1 and described herein.)

At an operation 76, the pressurized flow of breathable gas is controllably heated to maintain the pressurized flow of breathable gas at a target temperature based on a target humidity. The pressurized flow of breathable gas may be controllably heated responsive to the humidifier being controlled to extend the time the pressurized flow of breathable gas is humidified during the current usage session. In some embodiments, operation 76 is performed by a subject interface heater the same as or similar to subject interface heater 17 (shown in FIG. 1 and described herein.)

Although FIG. 1 shows many of the various components of system 10 as individual discrete components, many of those components may be integrally implemented in a humidifier. In such embodiments, the humidifier may include the various components of humidifier 21 that are shown in FIG. 1 as well as one or more additional components such as user interface 18, electronic storage 16, processor 22, liquid level sensors 19, and usage time sensors 20.

In some embodiments, system 10 may be configured to provide an alarm indication during humidifier set-up that would indicate to the user that an insufficient amount of water is in the humidifier for the patient's estimated usage time and/or sleeping time, thereby prompting the user to add more water.

In some embodiments, system 10 may be configured to enable the patient to select an estimated sleep duration by way of user interface 18.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure support system comprising:
a pressure generator configured to generate a pressurized flow of breathable gas for delivery to the airway of a subject;
a humidifier configured to hold a volume of liquid, and to controllably elevate a temperature of the liquid such that vapor formed from heated liquid humidifies the pressurized flow of breathable gas;
one or more usage time sensors configured to generate output signals conveying information related to the pressurized flow of breathable gas; and
one or more processors configured to execute computer program modules, the computer program modules comprising:
a liquid level module configured to obtain a level of the liquid held by the humidifier;
a usage time module configured to estimate a usage time of the subject for a current usage session, wherein estimating the usage time comprises:
determining that the subject has begun use of the system based on the output signals generated by the one or more usage time sensors;
generating an initial usage time estimate based on prior usage data for the subject from prior usage sessions; and
adjusting the initial usage time estimate based on the output signals generated by the one or more usage time sensors; and
a humidifier control module configured to control the humidifier to heat the liquid based on the estimated usage time for the current usage session and the level of the liquid held by the humidifier, thereby ensuring an amount of liquid will remain in the humidifier at the conclusion of the estimated usage time.

2. The system of claim 1, wherein the humidifier control module is further configured to adjust operation of the humidifier from an ordinary mode of operation to extend the time the pressurized flow of breathable gas is humidified during the current usage session.

3. The system of claim 2, wherein the system further comprises a subject interface heater configured to controllably heat the pressurized flow of breathable gas for delivery to the airway of a subject, and wherein the modules further comprise a subject interface heater control module configured to control the subject interface heater to maintain the temperature of the pressurized flow of breathable gas at a target temperature based on a target humidity determined by the humidifier control module.

4. The system of claim 1, wherein the usage time module is further configured to estimate the usage time of the subject for the current usage session based on the output signals generated by the one or more usage time sensors during the current usage session.

5. The system of claim 1, further comprising one or more liquid level sensors configured to generate output signals conveying information related to a current liquid level in the humidifier, wherein the liquid level module is configured to obtain the liquid level by determining a current liquid level based on the output signals generated by the one or more liquid level sensors, and, wherein the liquid level module is configured to determine a liquid usage rate based on the output signals generated by the one or more liquid level sensors.

6. The system of claim 1, wherein the humidifier control module is configured such that the amount of liquid will remain in the humidifier at the conclusion of the estimated usage time is selectable via a user interface of the system.

7. A method of delivering a humidity controlled pressurized flow of breathable gas to the airway of a subject with a pressure support system, the pressure support system comprising a pressure generator, a humidifier, one or more usage time sensors, and one or more processors configured to execute computer program modules, the computer program modules comprising a liquid level module, a usage time module, and a humidifier control module, the method comprising:
generating, with the pressure generator, a pressurized flow of breathable gas for delivery to the airway of a subject;
holding a volume of liquid in the humidifier;
controllably elevating, with the humidifier, a temperature of the liquid within the humidifier such that vapor formed from heated liquid humidifies the pressurized flow of breathable gas;
generating, with the one or more usage time sensors, one or more output signals conveying information related to the pressurized flow of breathable gas;
obtaining, with the liquid level module, a level of the liquid held by the humidifier;
estimating, with the usage time module, a usage time of the subject for a current usage session, wherein estimating the usage time comprises:
determining that the subject has begun use of the system based on the output signals generated by the one or more usage time sensors;
generating an initial usage time estimate based on prior usage data for the subject from prior usage sessions; and
adjusting the initial usage time estimate based on the output signals generated by the one or more usage time sensors; and
controlling, with the humidifier control module, the humidifier to heat the liquid based on the estimated usage time for the current usage session and the level of the liquid held by the humidifier, thereby ensuring an amount of liquid will remain in the humidifier at the conclusion of the estimated usage time.

8. The method of claim 7, further comprising adjusting, with the humidifier control module, the operation of the humidifier from an ordinary mode of operation to extend the time the pressurized flow of breathable gas is humidified during the current usage session.

9. The method of claim 8, wherein the method further comprises controllably heating, with a subject interface heater of the system, the pressurized flow of breathable gas and maintaining, with a subject interface heater control module of the one or more processors, the temperature of the pressurized flow of breathable gas at a target temperature based on a target humidity.

10. The method of claim 7, further comprising estimating, with the usage time module, the usage time of the subject for the current usage session based on the output signals generated by the one or more usage time sensors during the current usage session.

11. The method of claim 7, further comprising generating, with one or more liquid level sensors of the system, output signals conveying information related to a current liquid level in the humidifier, wherein the current liquid level is determined, by the liquid level module, based on the output signals conveying information related to the current liquid level, and wherein a liquid usage rate is determined, by the liquid level module, based on the output signals generated to convey information related to a current liquid level in the humidifier.

12. The method of claim 7, further comprising facilitating, with the humidifier control module, selection of the amount of liquid will remain in the humidifier at the conclusion of the estimated usage time via a user interface of the system.

13. A pressure support system comprising:
means for generating a pressurized flow of breathable gas for delivery to the airway of a subject;
means for holding a volume of liquid and controllably elevate a temperature of the liquid within the means for holding a volume of liquid such that vapor formed from heated liquid humidifies the pressurized flow of breathable gas;
means for generating output signals conveying information related to the pressurized flow of breathable gas;
means for obtaining a level of the liquid held by the means for humidifying;
means for estimating a usage time of the subject for a current usage session, wherein estimating the usage time comprises determining that that the subject has begun to use the system based on the output signals generated by the means for generating e output signals conveying information related to the pressurized flow of breathable gas, generating an initial usage time estimate based on prior usage data for the subject from prior usage sessions; and adjusting the initial usage time estimate based on the output signals generated by the one or more usage time sensors; and
means for controlling the means for humidifying to heat the liquid based on the estimated usage time for the current usage session and the level of the liquid held by the means for humidifying, thereby ensuring an amount of liquid will remain in the means for humidifying at the conclusion of the estimated usage time.

14. The system of claim 13, wherein the means for controlling the means for humidifying is further configured to adjust operation of the means for humidifying from an ordinary mode of operation to extend the time the pressurized flow of breathable gas is humidified during the current usage session.

15. The system of claim 14, wherein the system further comprises means for controllably heating the pressurized flow of breathable gas for delivery to the airway of a subject, and means for controlling the means for controllably heating the pressurized flow of breathable gas to maintain the temperature of the pressurized flow of breathable gas at a target temperature based on a target humidity determined by the means for controlling the means for humidifying.

16. The system of claim 13, wherein the means for estimating the usage time is further configured to estimate the usage time of the subject for the current usage session based on the output signals generated by the means for generating one or more output signals conveying information related to the pressurized flow of breathable gas during the current usage session.

17. The system of claim 13, further comprising means for generating output signals conveying information related to a current liquid level in the means for humidifying, wherein the means atoll for obtaining a level of the liquid held by the means for humidifying is configured to obtain the liquid level by determining a current liquid level based on the output signals generated by the means for generating one or more output signals conveying information related to a current liquid level in the means atoll for humidifying, and wherein the means atoll for obtaining a level of the liquid held by the means for humidify is configured to determine a liquid usage rate based on the output signals generated by the means for generating output signals conveying information related to a current liquid level in the means for humidifying.

18. The system of claim 13, further comprising means for facilitating selection of the amount of liquid that will remain in the humidifier at the conclusion of the estimated usage time via a user interface of the system.

* * * * *